(12) United States Patent
Lai et al.

(10) Patent No.: US 10,241,096 B2
(45) Date of Patent: Mar. 26, 2019

(54) NON-METHANE TOTAL HYDROCARBONS ANALYSIS APPARATUS AND METHOD FOR THE SAME

(71) Applicant: LIVE FRESH INC., Guangzhou (CN)

(72) Inventors: Ching-Chih Lai, Guangzhou (CN); Hao Fang, Guangzhou (CN); Yan Xiong, Guangzhou (CN)

(73) Assignee: LIVE FRESH INC. (CN)

( * ) Notice: Subject to any disclaimer, the term of this patent is extended or adjusted under 35 U.S.C. 154(b) by 454 days.

(21) Appl. No.: 15/009,866

(22) Filed: Jan. 29, 2016

(65) Prior Publication Data
US 2016/0363573 A1 Dec. 15, 2016

(30) Foreign Application Priority Data

Jun. 11, 2015 (CN) .......................... 2015 1 0318957

(51) Int. Cl.
*G01N 33/00* (2006.01)
*B01L 3/00* (2006.01)

(52) U.S. Cl.
CPC .......... *G01N 33/0047* (2013.01); *B01L 3/561* (2013.01); *B01L 3/567* (2013.01)

(58) Field of Classification Search
None
See application file for complete search history.

(56) References Cited

U.S. PATENT DOCUMENTS

| | | | | |
|---|---|---|---|---|
| 3,650,090 A | * | 3/1972 | Temple | G01N 1/405 73/23.39 |
| 2003/0172718 A1 | * | 9/2003 | Lee | G01N 30/20 73/23.41 |
| 2005/0053522 A1 | * | 3/2005 | King | C25D 21/12 422/68.1 |

* cited by examiner

*Primary Examiner* — Matthew D Krcha
(74) *Attorney, Agent, or Firm* — Schmeiser, Olsen & Watts, LLP

(57) ABSTRACT

A non-methane total hydrocarbons analysis apparatus and method are introduced. The analysis apparatus includes a six-pass valve, quantification ring, first stored gas pipe, second stored gas pipe, multi-pass valve, molecular sieve filling pipe, first air source, and detector. The six-pass valve and the multi-pass valve are configured to have a load status bit. A gas under test passes through the molecular sieve to remove non-methane total hydrocarbons such that the treated gas functions as a background gas for filling the first stored gas pipe and the second stored gas pipe. The six-pass valve and the multi-pass valve are configured to have an entered sample status bit such that zero-grade compressed air drives the gas inside the second stored gas pipe, quantification ring, and first stored gas pipe to enter the detector. The background gas inside the second stored gas pipe and the second stored gas pipe provides a baseline.

34 Claims, 2 Drawing Sheets

NON-METHANE TOTAL HYDROCARBONS ANALYSIS APPARATUS AND METHOD FOR THE SAME

CROSS-REFERENCE TO RELATED APPLICATION

This non-provisional application claims priority under 35 U.S.C. § 119(a) on Patent Application No(s). 201510318957.5 filed in China on Jun. 11, 2015, the entire contents of which are hereby incorporated by reference.

FIELD OF TECHNOLOGY

The present invention relates to methods of detecting a gas and, more particularly, to a non-methane total hydrocarbons analysis apparatus and a method for the same.

BACKGROUND

Methane ($CH_4$) and non-methane total hydrocarbons (NMHC) abound in nature, especially the atmosphere where $CH_4$ and NMHC demonstrate concentrations of approximately 1.8 ppmv and 30 ppbv, respectively. The term non-methane total hydrocarbons (NMHC) refers to all hydrocarbons except methane and features extremely complicated compositions which mainly originate from combustion of gasoline, ignition of rubbish, evaporation of solvents, and the refining of waste. When existing in the atmosphere and exceeding a specific concentration, NMHC is not only harmful to the health of human beings but also gives rise to chemical smog upon exposure to sunlight under certain conditions to thereby bring about hazards to the environment and human beings.

Considering a wide variety of hazards caused by NMHC in the atmosphere, it is necessary to exercise real-time surveillance and control over pollutant sources, roads with heavy traffic, industrial parks and factories in terms of NMHC concentrations. The surveillance of NMHC content in the air began in the $20^{th}$ century overseas by condensation-weight technique, combustion technique, and infrared spectrophotometry. Nonetheless, all these techniques have their own drawbacks, such as limits of use and intricate operation, and thus is never widely applied.

Nowadays, the detection and measurement of NMHC is carried out in various ways, including undergoing oxidation and reduction to $CH_4$ before being detected and measured, undergoing oxidation and conversion to remove non-methane total hydrocarbons, and undergoing gas chromatography.

The aforesaid technique of converting NMHC into $CH_4$ before being detected and measured involves carrying out semi-automated analysis of NMHC by following the steps described below. The gases CO, $CO_2$ and $CH_4$ are extracted from non-methane organic matters with a chromatography column. Then, the extracted non-methane total hydrocarbons are oxidized to become $CO_2$, and the $CH_4$ is restored by reduction, which are then measured with a $CH_4$-oriented FID detector to thereby calculate the non-methane total hydrocarbon content. However, the aforesaid technique has its own drawbacks. First, the measurement process is subject to interference from $CO_2$ and water. Second, the method requires catalytic oxidizing agents and reducing agents, and thus it is necessary to ensure that, during the online surveillance process, the oxidation rate of converting the non-methane total hydrocarbons into $CO_2$ by oxidation and the reduction rate of converting $CO_2$ into $CH_4$ by reduction must be placed under intricate systemic control, thereby affecting the analysis process greatly.

The aforesaid technique of undergoing oxidation and conversion to remove non-methane total hydrocarbons is described as follows: a sample gas enters an analysis instrument through an admission pipeline, passes through a high temperature conversion furnace, wherein the high temperature conversion furnace is loaded with a conversion agent whereby all the non-methane total hydrocarbons of the sample gas are completely destroyed at 150-250° C., such that only the residual methane will undergo the test. Another gas route does not require the sample gas to pass through the high temperature conversion furnace, such that the gas being monitored contains all the substances, that is, total hydrocarbons. Given the timed switching of an electromagnetic valve, the two gas routes eventually undergo a hydrogen flame ionization detector test to thereby yield the methane concentration and the total hydrocarbon concentration, respectively. The difference in readings between the two gas routes equals the non-methane total hydrocarbon content. During the above process, a high temperature conversion furnace is required and adapted to destroy all the non-methane total hydrocarbons; however, the result of the test depends greatly on the degree of conversion and destruction of the non-methane total hydrocarbons during the above process.

Gas chromatography manifests much flexibility and is generally divided into two categories, namely total hydrocarbon-methane indirect test method and methane-non-methane total hydrocarbon direct test method.

The total hydrocarbon-methane indirect test method is in wide use and requires a sample gas to follow two routes, that is, one which involves measuring the total hydrocarbon content with the FID detector directly, and the other which involves passing the sample gas through a methane molecular sieve so as to remove high-carbon hydrocarbons, measuring the methane content with the FID detector, and eventually subtracting the methane content from the total hydrocarbon content to obtain the non-methane total hydrocarbon content. This method is recommended by China's Environmental Protection Administration (EPA) for use in measuring non-methane total hydrocarbon content and monitoring pollution sources which produce non-methane total hydrocarbons.

However, this method has its own drawbacks. For example, it requires subtraction when measuring the non-methane total hydrocarbon content, that is, subtracting the methane content from the total hydrocarbon content to therefore obtain the non-methane total hydrocarbon content. The basic methane concentration in the air sample is typically 1.8 ppmv approximately. If the basic non-methane hydrocarbon concentration in the air sample is much less than the basic methane concentration in the air sample, that is, when the methane concentration approaches the total hydrocarbons concentration (THC), the direct subtraction will bring about the addition of the errors of the readings, and in consequence the data error of the non-methane total hydrocarbons at a very low concentration increases.

On the other hand, the methane-non-methane direct test method is carried out by following the steps described below. The sample gas is adsorbed with an adsorption pipe. The methane passes through the adsorption pipe and then undergoes reverse desorption at the adsorption pipe. The organic matters which have undergone decomposition and desorption are indicative of the non-methane total hydrocarbon content. After the sample gas thus entered has undergone the quantification process performed in just one single instance with a quantification pipe, the test conducted on the methane and non-methane total hydrocarbons is done. This method is easy to carry out. However, the result of the monitoring of non-methane total hydrocarbons depends directly on such factors as to whether the desorption and reversing processes are carried out thoroughly to heavy non-methane organic matters at a constant temperature when the monitoring process is carried out continuously; as a result, the readings of the non-methane total hydrocarbon content tend to be low. In addition, the aforesaid thermal decomposition process necessitates high requirements for a thermal decomposition pipe and thus is susceptible to cross pollution.

With all things considered, it is necessary to provide a highly sensitive and highly stable online analysis method and apparatus which yield accurate surveillance results and are easy to operate in performing real-time online surveillance on airborne non-methane total hydrocarbons at pollutant sources, roads with heavy traffic, industrial parks and factories.

SUMMARY

In view of the aforesaid drawbacks of the prior art, it is an objective of the present invention to provide a non-methane total hydrocarbons analysis apparatus and a method for the same. The apparatus and method are conducive to accurate and stable detection of the non-methane total hydrocarbons and achieve a measurement limit of less than 0.1 mg/m$^3$.

A non-methane total hydrocarbons analysis apparatus comprises a six-pass valve, a quantification ring, a first stored gas pipe, a second stored gas pipe, a multi-pass valve, a molecular sieve filling pipe, a first air source and a detector.

The six-pass valve has a sample entering hole, a multi-pass valve interface, a quantification ring first interface, a first stored gas pipe outlet, a second stored gas pipe interface and a quantification ring second interface. The multi-pass valve comprises a first air admission hole, a first discharge hole, a six-pass valve interface, a molecular sieve first interface, a molecular sieve second interface, and a first stored gas pipe inlet.

The quantification ring second interface, the quantification ring and the quantification ring first interface are in communication with each other successively. The multi-pass valve interface is in communication with the six-pass valve interface through a pipeline. The molecular sieve first interface, the molecular sieve filling pipe and the molecular sieve second interface are in communication successively through a pipeline. The first stored gas pipe inlet, the first stored gas pipe, the first stored gas pipe outlet, the second stored gas pipe interface, the second stored gas pipe, and the detector are in communication successively through a pipeline. The first air source is in communication with the first air admission hole.

The six-pass valve has a load status bit and an entered sample status bit. When the six-pass valve is disposed at the load status bit, the sample entering hole is in communication with quantification ring second interface, and the multi-pass valve interface is in communication with quantification ring first interface, wherein the first stored gas pipe outlet is in communication with the second stored gas pipe interface. When the six-pass valve is disposed at the entered sample status bit, the sample entering hole is in communication with the multi-pass valve interface, and the quantification ring first interface is in communication with the first stored gas pipe outlet, wherein the second stored gas pipe interface is in communication with quantification ring second interface.

In the embodiment where the multi-pass valve has the load status bit and the entered sample status bit, when multi-pass valve is disposed at the load status bit, the first air admission hole is in communication with the first discharge hole, and the six-pass valve interface is in communication with the molecular sieve first interface, wherein the molecular sieve second interface is in communication with the first stored gas pipe inlet; when the multi-pass valve is disposed at the entered sample status bit, the first discharge hole is in communication with six-pass valve interface, and the first stored gas pipe inlet is in communication with the first air admission hole.

The aforesaid non-methane total hydrocarbon analysis apparatus requires that the gas under test be passed through the molecular sieves to thereby remove the non-methane total hydrocarbons and then function as a background gas which fills the first stored gas pipe and the second stored gas pipe. Then, with a conversion process carried out with the six-pass valve and the multi-pass valve, zero-grade compressed air drives the gas inside the second stored gas pipe, the quantification ring, and the first stored gas pipe to enter the detector successively such that the background gas inside the second stored gas pipe and the first stored gas pipe functions as a baseline, and displays the head and tail of the spectral peak of the gas under test which is disposed at the quantification ring. Hence, the operation of the aforesaid non-methane total hydrocarbon analysis apparatus circumvents the aforesaid drawbacks of the prior art, that is, when the methane concentration approaches the total hydrocarbons concentration, direct subtraction brings about the addition of the errors of reading errors, and the analysis and test processes are subject to interference from $CO_2$ and water. As a result, the operation of the aforesaid non-methane total hydrocarbon analysis apparatus dispenses with the need to give consideration to the oxidation rate and the reduction rate and thus enhance the accuracy in the test results, not to mention that it advantageously features reliable principles and stable methodology.

In one of the embodiments, the multi-pass valve is provided in the form of an eight-pass valve. The eight-pass valve further has the second discharge hole and the second air admission hole. The analysis apparatus further comprises the second air source, and the second air source is in communication with the second air admission hole.

When the eight-pass valve is disposed at the load status bit, the second discharge hole is in communication with the second air admission hole. When the eight-pass valve is disposed at the entered sample status bit, the molecular sieve first interface is in communication with the second discharge hole, and the second air admission hole is in communication with molecular sieve second interface.

Given the above configuration, the second air source is used to perform a reversing process on the molecular sieves such that the adsorbed non-methane substances undergo decomposition at a constant temperature before being discharged through the second discharge hole, so as to prevent the molecular sieves from adsorption saturation and extend the service life of the molecular sieves.

In one of the embodiments, the second flow control system is disposed at the pipeline connected between the second air source and the second air admission hole. Given the second flow control system and strict control of the reversing gas flow rate, the aforesaid composition occurs efficiently.

In one of the embodiments, the first pressure gauge is disposed at the pipeline connected between the multi-pass valve interface and the six-pass valve interface, and the second pressure gauge is disposed at the pipeline connected between the first air source and the first air admission hole, wherein the third pressure gauge is disposed at the pipeline connected between the second air source and the second air admission hole. With a pressure gauge, it is feasible to monitor the pressures at each of the pipelines of the analysis apparatus in real time to thereby ensure that the ongoing analysis process will be stable.

In one of the embodiments, the first flow control system is disposed at the pipeline connected between the multi-pass valve interface and the six-pass valve interface. Given the first flow control system and strict control of the gas feeding rate of the gas under test, it is practicable to effectuate adsorption efficiently.

In one of the embodiments, an air pneumatic pump is disposed at the pipeline connected between the multi-pass valve interface and the first flow control system. The air pneumatic pump drives the gas under test to flow from the multi-pass valve interface toward the six-pass valve interface.

In one of the embodiments, a back pressure valve is disposed at the pipeline connected between the air pneumatic pump and the first flow control system. The back pressure valve has a shunting exhaust vent. The back pressure valve ensures that the gas which exits the front end of the back pressure valve to enter the pipeline through the outlet of the air pneumatic pump will be kept in a state of a stable pressure, such that the sample gas is always flowing steadily and redundant gas can be discharged from the shunting exhaust vent.

In one of the embodiments, the detector is provided in the form of a hydrogen flame ionization detector (FID), and the analysis apparatus further comprises a hydrogen gas source and a detection air source which are connected to the detector. The FID detector has such advantages as simple structure, high stability, high sensitivity and quick response.

In one of the embodiments, the molecular sieve filling pipe contains therein molecular sieves with an effective aperture of 5 Å. The molecular sieves with the aforesaid aperture demonstrate satisfactory adsorption effect.

The present invention further discloses a non-methane total hydrocarbons analysis method which is applied to the aforesaid analysis apparatus and comprises the steps described as follows:

1) configuring a six-pass valve and a multi-pass valve to have a load status bit each, conveying a gas under test from a sample entering hole to the six-pass valve, passing the gas through the quantification ring second interface and the quantification ring successively to thereby fill the quantification ring with the gas, conveying the gas from the quantification ring first interface to the six-pass valve, conveying the gas to a six-pass valve interface through a multi-pass valve interface, conveying the gas to a molecular sieve filling pipe through a molecular sieve first interface, wherein non-methane total hydrocarbons in the gas are adsorbed and filtered out by the molecular sieve to therefore produce a background gas which contains methane hydrocarbons only, and then the background gas enters the multi-pass valve again through the molecular sieve second interface, enters a first stored gas pipe through a first stored gas pipe inlet, and fills the first stored gas pipe, wherein, thereafter, the background gas passes through the first stored gas pipe outlet and a second stored gas pipe interface successively, enters a second stored gas pipe, fills the second stored gas pipe and eventually enters the detector; and 2) configuring the six-pass valve and the multi-pass valve to have an entered sample status bit each, passing a zero-grade air from the first air source to the multi-pass valve through the first air admission hole, conveying the zero-grade air to the detector through the first stored gas pipe inlet, the first stored gas pipe, the first stored gas pipe outlet, the quantification ring first interface, the quantification ring, the quantification ring second interface, the second stored gas pipe interface, and the second stored gas pipe successively, conveying the background gas from the second stored gas pipe to the detector, conveying the gas under test from the quantification ring to the detector, and conveying the background gas from the first stored gas pipe to the detector, such that the background gas which contains methane hydrocarbons only is detected to thereby function as a baseline of a non-methane total hydrocarbons chromatographic peak.

The aforesaid non-methane total hydrocarbons analysis method requires that the gas under test be passed through the molecular sieves to thereby remove the non-methane total hydrocarbons and then function as a background gas which fills the first stored gas pipe and the second stored gas pipe. Then, with a conversion process carried out with the six-pass valve and the multi-pass valve, zero-grade compressed air drives the gas inside the second stored gas pipe, the quantification ring, and the first stored gas pipe to enter the detector successively such that the background gas inside the second stored gas pipe and the first stored gas pipe functions as a baseline, and displays the head and tail of the spectral peak of the gas under test which is disposed at the quantification ring. Hence, the operation of the aforesaid non-methane total hydrocarbon analysis apparatus circumvents the aforesaid drawbacks of the prior art, that is, when the methane concentration approaches the total hydrocarbons concentration, direct subtraction brings about the addition of the errors of reading errors, and the analysis and test processes are subject to interference from $CO_2$ and water. As a result, the operation of the aforesaid non-methane total hydrocarbon analysis apparatus dispenses with the need to give consideration to the oxidation rate and the reduction rate and thus enhance the accuracy in the test results, not to mention that it advantageously features reliable principles and stable methodology.

In one of the embodiments, the non-methane total hydrocarbons analysis method is characterized in that: the analysis apparatus of claim 2 is required, and, in step 2), the zero-grade air of the second air source is conveyed to the eight-pass valve through the second air admission hole and conveyed to molecular sieves through the molecular sieve second interface to thereby perform reverse decomposition on the molecular sieves, remove the adsorbed non-methane total hydrocarbons, and discharge the non-methane total hydrocarbons-containing air through the molecular sieve first interface and the second discharge hole. By performing reverse decomposition on the molecular sieves and cleansing the molecular sieves, it is practicable to extend the service life of the molecular sieves.

Compared with the prior art, the present invention has the following advantages:

A non-methane total hydrocarbons analysis apparatus of the present invention is characterized in that: given a sophisticated arrangement of a six-pass valve, a multi-pass valve, a first stored gas pipe, a second stored gas pipe, and molecular sieves, it is feasible to configure both the six-pass valve and multi-pass valve to have the load status bit such that a gas under test has non-methane total hydrocarbons removed therefrom with the molecular sieves to subsequently function as a background gas for filling the first stored gas pipe and the second stored gas pipe; then, with a conversion process carried out with the six-pass valve and multi-pass valve, both the six-pass valve and multi-pass valve are configured to have the entered sample status bit such that zero-grade compressed air drives the gas to enter the detector through the second stored gas pipe, the quantification ring, and the first stored gas pipe successively, and thus the background gas inside the second stored gas pipe and the first stored gas pipe functions as a baseline, and displays the head and tail of the spectral peak of the gas under test which is disposed at the quantification ring. Hence, the operation of the aforesaid non-methane total hydrocarbon analysis apparatus circumvents the aforesaid drawbacks of the prior art, that is, when the methane concentration approaches the total hydrocarbons concentration, direct subtraction brings about the addition of the errors of reading errors, and the analysis and test processes are subject to interference from $CO_2$ and water. As a result, the operation of the aforesaid non-methane total hydrocarbon analysis apparatus dispenses with the need to give consideration to the oxidation rate and the reduction rate and thus enhance the accuracy in the test results, not to mention that it advantageously features reliable principles, stable methodology, and achieving a measurement limit of less than 0.1 $mg/m^3$.

BRIEF DESCRIPTION

DETAILED DESCRIPTION

Embodiment 1

Figure 1:
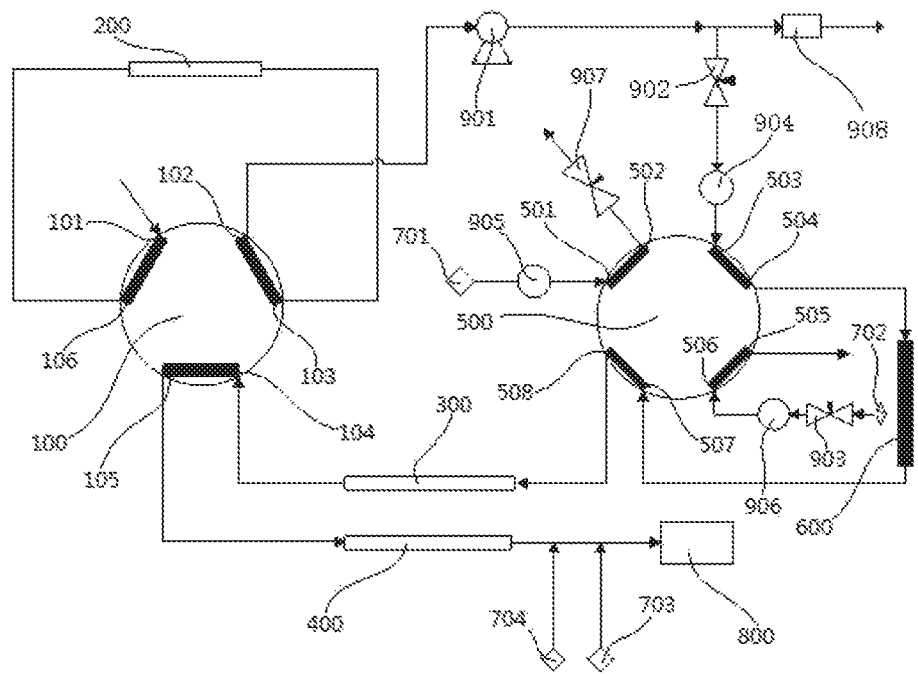
FIG. 1 is a schematic view of the structure and the gas route with a load status bit applied to both a six-pass valve and an eight-pass valve.
Figure 2:
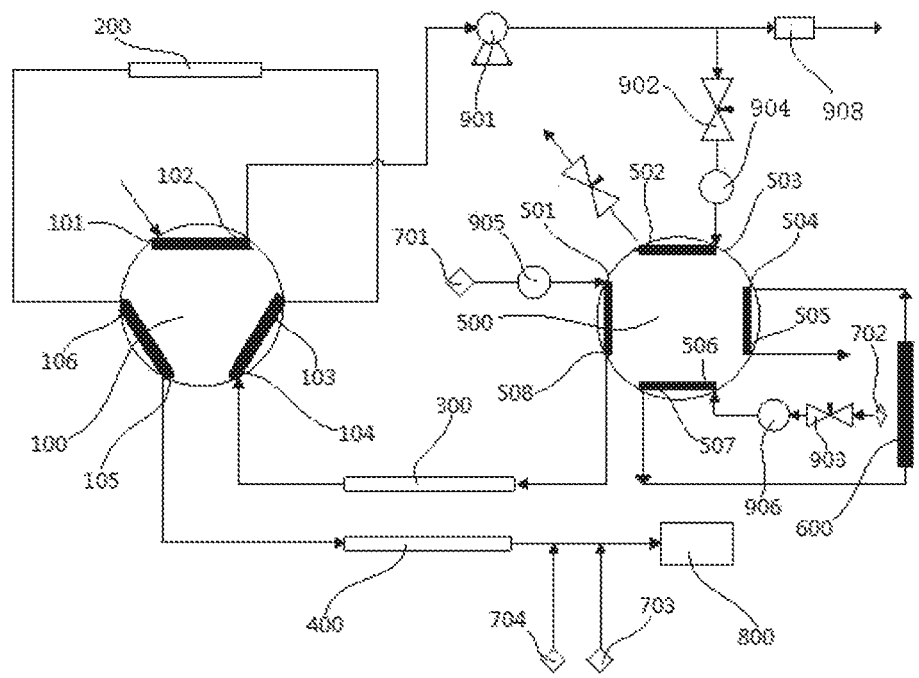
FIG. 2 is a schematic view of the structure and the gas route with an entered sample status bit applied to both the six-pass valve and the eight-pass valve.

Referring to FIGS. 1-2, a non-methane total hydrocarbons analysis apparatus comprises a six-pass valve 100, a quantification ring 200, a first stored gas pipe 300, a second stored gas pipe 400, a multi-pass valve, a molecular sieve filling pipe 600, a first air source 701 and a detector 800. In this embodiment, the multi-pass valve is an eight-pass valve 500.

The six-pass valve 100 has a sample entering hole 101, a multi-pass valve interface 102, a quantification ring first interface 103, a first stored gas pipe outlet 104, a second stored gas pipe interface 105 and a quantification ring second interface 106. The eight-pass valve 500 has a first air admission hole 501, a first discharge hole 502, a six-pass valve interface 503, a molecular sieve first interface 504, a molecular sieve second interface 507, a first stored gas pipe inlet 508, a second discharge hole 505, and a second air admission hole 506.

The quantification ring second interface 106, the quantification ring 200, the quantification ring first interface 103 are in communication with each other successively. The multi-pass valve interface 102 is in communication with the six-pass valve interface 503 through a pipeline. In this embodiment, an air pneumatic pump 901, a back pressure valve 908 and a first flow control system 902 are successively disposed along the pipeline which connects the multi-pass valve interface 102 and the six-pass valve interface 503. The back pressure valve 908 has a shunting exhaust vent for ensuring that the gas which exits the front end of the back pressure valve 908 and leaves the outlet of the air pneumatic pump 901 for the pipeline will be kept at a stable level of pressure. The molecular sieve first interface 504, the molecular sieve filling pipe 600, and the molecular sieve second interface 507 are in communication successively through a pipeline. The first stored gas pipe inlet 508, the first stored gas pipe 300, the first stored gas pipe outlet 104, the second stored gas pipe interface 105, the second stored gas pipe 400, and the detector 800 are in communication successively through a pipeline. The first air source 701 is in communication with the first air admission hole 501. In this embodiment, the analysis apparatus further comprises the second air source 702. The second air source 702 is in communication with the second air admission hole 506. A second flow control system 903 is disposed at the pipeline connected between the second air source 702 and the second air admission hole 506. The first discharge hole 502 is further connected to a third flow control system 907.

In this embodiment, a first pressure gauge 904 is disposed at the pipeline connected between the multi-pass valve interface 102 and the six-pass valve interface 503. A second pressure gauge 905 is disposed at the pipeline connected between the first air source 701 and the first air admission hole 501. A third pressure gauge 906 is disposed at the pipeline connected between the second air source 702 and the second air admission hole 506.

In this embodiment, the detector 800 is a hydrogen flame ionization detector (FID), and the analysis apparatus further comprises a hydrogen gas source 704 and a detection air source 703 which are connected to the detector. Understandably, it is feasible to select any other detectors in accordance with the properties and test requirements of the target to be detected; however, the FID detector thus selected demonstrates high sensitivity and stability toward organic matters and thus is suitable for use with the tests conducted on the hydrocarbons applicable to this embodiment.

In this embodiment, the molecular sieve filling pipe 600 contains molecular sieves with an effective aperture of 5 Å. Understandably, it is feasible to select molecular sieves with an appropriate mesh diameter in accordance with the molecular weights of the substances to be intercepted; however, the molecular sieves with an effective aperture are effective in adsorbing non-methane total hydrocarbons.

The six-pass valve 100 has a load status bit and an entered sample status bit. When the six-pass valve is disposed at the load status bit, as shown in FIG. 1, the sample entering hole 101 is in communication with the quantification ring second interface 106, and the multi-pass valve interface 102 is in communication with the quantification ring first interface 103, wherein the first stored gas pipe outlet 104 is in communication with the second stored gas pipe interface 105. When the six-pass valve is disposed at the entered sample status bit, as shown in FIG. 2, the sample entering hole 101 is in communication with the multi-pass valve interface 102, and the quantification ring first interface 103 is in communication with the first stored gas pipe outlet 104, wherein the second stored gas pipe interface 105 is in communication with the quantification ring second interface 106.

The eight-pass valve 500 has the load status bit and the entered sample status bit. When the eight-pass valve is disposed at the load status bit, as shown in FIG. 1, the first air admission hole 501 is in communication with the first discharge hole 502, and the six-pass valve interface 503 is in communication with the molecular sieve first interface 504, wherein the second discharge hole 505 is in communication with the second air admission hole 506, whereas the molecular sieve second interface 507 is in communication with the first stored gas pipe inlet 508. When the multi-pass valve is disposed at the entered sample status bit, as shown in FIG. 2, the first discharge hole 502 is in communication with the six-pass valve interface 503, and the first stored gas pipe inlet 508 is in communication with the first air admission hole 501, wherein the molecular sieve first interface 504 is in communication with the second discharge hole 505, whereas the second air admission hole 506 is in communication with the molecular sieve second interface 507.

In this embodiment, the multi-pass valve is provided in the form of the eight-pass valve to thereby not only conduct a test but also perform reverse decomposition on the molecular sieves and cleanse the molecular sieves. Understandably, in the situation where conducting the test is the one and only one purpose, it is feasible to provide the multi-pass valve in the form of the six-pass valve and thus dispense with the second discharge hole 505, the second air admission hole 506, and the second air source 702, without compromising the basic principles of the test, albeit at the cost of jeopardizing the adsorption effect and shortening the service life of the molecular sieves.

The non-methane total hydrocarbons are analyzed with the non-methane total hydrocarbons analysis apparatus of this embodiment by following the steps described below.

1) configuring both the six-pass valve 100 and the eight-pass valve 500 to have the load status bit, as shown in FIG. 1, with reference to arrows which indicate the related directions, respectively, conveying the gas under test from the sample entering hole 101 to the six-pass valve 100, passing the gas under test through the quantification ring second interface 106 and the quantification ring 200 successively, filling the quantification ring 200 with the gas under test, conveying the gas under test from the quantification ring first interface 103 to the six-pass valve 100 again, conveying the gas under test to the six-pass valve interface 503 through the multi-pass valve interface 102, conveying the gas under test to the molecular sieve filling pipe 600 through the molecular sieve first interface 504, such that the non-methane total hydrocarbons in the gas under test are adsorbed and filtered out by the molecular sieves so as to produce a background gas which contains methane hydrocarbons only. Afterward, the background gas is conveyed from the molecular sieve second interface 507 to the eight-pass valve 500 again and then conveyed to the first stored gas pipe 300 through the first stored gas pipe inlet 508 so as to fill the first stored gas pipe 300. Then, the background gas is conveyed to the second stored gas pipe 400 through the first stored gas pipe outlet 104 and the second stored gas pipe interface 105 successively so as to fill the second stored gas pipe 400 before entering the detector 800.

Figure 3:
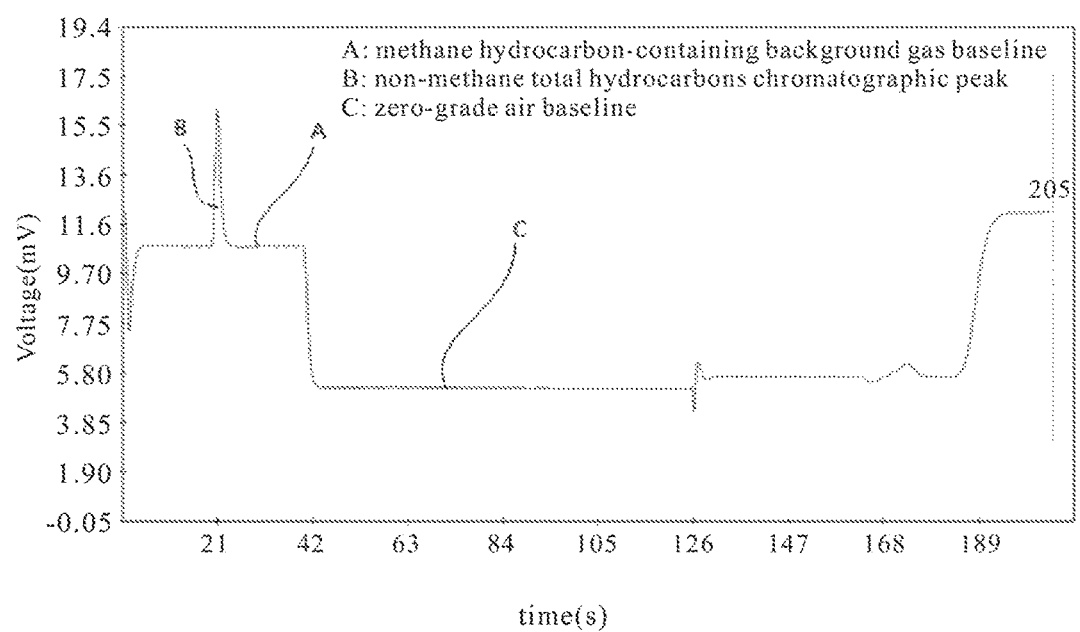
FIG. 3 is a diagram of the analysis of a sample obtained in an embodiment.

2) configuring both the six-pass valve 100 and the eight-pass valve 500 to have the entered sample status bit, as shown in FIG. 2, with reference to arrows which indicate the related directions, respectively, conveying a zero-grade air from the first air source 701 to the eight-pass valve 500 through the first air admission hole 501, conveying the zero-grade air to the detector 800 through the first stored gas pipe inlet 508, the first stored gas pipe 300, the first stored gas pipe outlet 104, the quantification ring first interface 103, the quantification ring 200, the quantification ring second interface 106, the second stored gas pipe interface 105, and the second stored gas pipe 400 successively to thereby allow the background gas from the second stored gas pipe 400 to enter the detector 800 first. Thereafter, the gas under test in the quantification ring 200 enters the detector 800. Then, the background gas in the first stored gas pipe 300 enters the detector 800. Eventually, the background gas which contains methane hydrocarbons is detected to thereby function as a baseline of a non-methane total hydrocarbons chromatographic peak, as shown in FIG. 3.

The methane content of the gas under test equals the methane content of the background gas; hence, each peak level shown in the chromatogram reflects the non-methane total hydrocarbons (NMHC) exactly to thereby render it unnecessary to give consideration to the methane content, nor does it amplify an analysis error.

When both the six-pass valve 100 and the eight-pass valve 500 are configured to have the entered sample status bit, the zero-grade air of the second air source 702 is conveyed to the eight-pass valve 500 through the second air admission hole 506 and then conveyed to the molecular sieve filling pipe 600 through the molecular sieve second interface 507 to thereby perform reverse decomposition on the molecular sieves and remove the adsorbed non-methane total hydrocarbons before being discharged through the molecular sieve first interface 504 and the second discharge hole 505. By performing reverse decomposition on the molecular sieves and cleansing the molecular sieves, it is practicable to extend the service life of the molecular sieves.

With the aforesaid analysis apparatus and analysis method, the test is conducted on propane with gas samples of standard gas concentration of 2 mg/m$^3$. Both the first stored gas pipe and the second stored gas pipe are made of stainless steel and are 10 m long. The quantification ring, the stored gas pipe, the molecular sieves, and the other systemic components operate at a constant temperature of 150□. Samples are entered in a shunt-free manner at a rate of 1 ml each time, with a gas flow rate of 35 ml/min, wherein the FID detector operates at a temperature of 200□. The test is performed 12 times in total, and the test results are shown in the table below.

TABLE 1 propane standard gas test data

| peak area (mv) | | | | | | peak area mean (mv) | standard deviation |
|---|---|---|---|---|---|---|---|
| 0.00641 | 0.00627 | 0.00644 | 0.00631 | 0.00638 | 0.00625 | 0.006361 | 8.98 × 10$^{-5}$ |
| 0.0065 | 0.00633 | 0.0063 | 0.0065 | 0.00639 | 0.00625 | | |

The apparatus measurement limit is calculated with the formula below.

$$D_L = KS_0 \times C/X$$

$D_L$: apparatus measurement limit;
k: confidence factor, preferably 3;
$S_0$: sample reading standard deviation;

C: content of substance under test;

X: sample reading mean.

The calculation yields a propane standard gas least measurement limit of 0.085 mg/m3, and the test result exhibits satisfactory parallelism, with a standard deviation as low as $8.98 \times 10^{-5}$.

A comparison of the non-methane total hydrocarbons analysis method of this embodiment and various methods of the prior art shows that the various methods of the prior art mostly resort to subtraction in order to indirectly calculate the content of non-methane total hydrocarbons (NMHC). Considering that no test process is immune from errors, when the methane concentration approaches the total hydrocarbons concentration (THC), there is addition of errors arising from the non-methane total hydrocarbon concentrations calculated by subtraction, as illustrated with the example below.

When $C_{THC}=1.4\pm0.07$ mg/m$^3$ (with an error of 5%), and $C_{CH4}=1.3\pm0.07$ mg/m$^3$ (with an atmospheric background parameter set to 1.3 mg/m$^3$, with an error of 5%), the equation $C_{NMHC}=C_{THC}-C_{CH4}$ yields $C_{NMHC}=0.1\pm0.14$ mg/m$^3$ (with an error of 140%), thereby indicating that the actual concentration of the non-methane total hydrocarbons falls exactly within a wide test error range and thus leads to inaccuracy, nor is the test limit of 0.1 mg/m$^3$ achievable.

To effect a reasonable error range, it is feasible to infer a reasonable error range of 5%-10% for the $C_{NMHC}$ concentration. Given $C_{THC}=1.4$ mg/m$^3$, the error range reaches 0.07 mg/m$^3$ and 0.14 mg/m$^3$. Since $C_{THC}>C_{CH4}$ and $C_{CH4}$ is unknown, the error of $C_{THC}$ is used to infer that the reasonable test concentration (within an allowable error of 10%) of $C_{NMHC}$ falls between 0.7 mg/m$^3$-1.4 mg/m$^3$. Hence, it is practicable to infer that the test limits of the methods based on subtraction as disclosed in the prior art can only reasonably achieve 1 mg/m$^3$ approximately. With the aforesaid analysis apparatus, analysis method and analysis criteria, the result of the tests performed on gas samples of the toluene standard gas concentration of 0.2 mg/m$^3$ is shown in the table below.

TABLE 2 toluene standard gas test data

| peak area (mv) | | | | | | peak area mean (mv) | standard deviation |
|---|---|---|---|---|---|---|---|
| 0.000742 | 0.000733 | 0.000809 | 0.000688 | 0.000721 | 0.000743 | 0.000727 | $8.14 \times 10^{-5}$ |
| 0.000935 | 0.000623 | 0.000689 | 0.000646 | 0.000705 | 0.000689 | | |

The calculation carried out in accordance with embodiment 1 shows that the aforesaid toluene standard gas least measurement limit is 0.067 mg/m$^3$, and the test result exhibits satisfactory parallelism, with a standard deviation as low as $8.14 \times 10^{-5}$. The aforesaid technical features of the embodiment can be combined at will. To render the description concise, the description omits all possible combinations of the technical features of the embodiment. However, the combinations of the technical features must be interpreted to fall within the claims of the present invention, provided that they are not contradictory.

The present invention is disclosed above by preferred embodiments. However, persons skilled in the art should understand that the preferred embodiments are illustrative of the present invention only, but should not be interpreted as restrictive of the scope of the present invention. Hence, all equivalent modifications and replacements made to the aforesaid embodiments should fall within the scope of the present invention. Accordingly, the legal protection for the present invention should be defined by the appended claims.

What is claimed is:

1. A non-methane total hydrocarbons analysis apparatus, comprising a six-pass valve, a quantification ring, a first stored gas pipe, a second stored gas pipe, a multi-pass valve, a molecular sieve filling pipe, a first air source and a detector, wherein the six-pass valve has a sample entering hole, a multi-pass valve interface, a quantification ring first interface, a first stored gas pipe outlet, a second stored gas pipe interface and a quantification ring second interface, wherein the multi-pass valve comprises a first air admission hole, a first discharge hole, a six-pass valve interface, a molecular sieve first interface, a molecular sieve second interface and a first stored gas pipe inlet, wherein the quantification ring second interface, the quantification ring and the quantification ring first interface are in communication successively, wherein the multi-pass valve interface is in communication with the six-pass valve interface through a pipeline, wherein the molecular sieve first interface, the molecular sieve filling pipe and the molecular sieve second interface are in communication successively through a pipeline, wherein the first stored gas pipe inlet, the first stored gas pipe, the first stored gas pipe outlet, the second stored gas pipe interface, the second stored gas pipe and the detector are in communication successively through a pipeline, wherein the first air source is in communication with the first air admission hole, wherein the six-pass valve has a load status bit and an entered sample status bit, with the load status bit allowing the sample entering hole to be in communication with the quantification ring second interface, the multi-pass valve interface to be in communication with the quantification ring first interface, and the first stored gas pipe outlet to be in communication with the second stored gas pipe interface, and with the entered sample status bit allowing the sample entering hole to be in communication with the multi-pass valve interface, the quantification ring first interface to be in communication with the first stored gas pipe outlet, and the second stored gas pipe interface to be in communication with the quantification ring second interface, wherein the multi-pass valve has a load status bit and an entered sample status bit, with the load status bit allowing the first air admission hole to be in communication with the first discharge hole, the six-pass valve interface to be in communication with the molecular sieve first interface, and the molecular sieve second interface to be in communication with the first stored gas pipe inlet, and with the entered sample status bit allowing the first discharge hole to be in communication with the six-pass valve interface, and the first stored gas pipe inlet to be in communication with the first air admission hole.

2. The non-methane total hydrocarbons analysis apparatus of claim 1, characterized in that: the multi-pass valve is an eight-pass valve provided with the second discharge hole and the second air admission hole, wherein the analysis apparatus further comprises a second air source in communication with the second air admission hole,
wherein the load status bit of the eight-pass valve allows the second discharge hole to be in communication with the second air admission hole, and the entered sample status bit of the eight-pass valve allows the molecular sieve first interface to be in communication with the second discharge hole and allows the second air admission hole to be in communication with the molecular sieve second interface.

3. The non-methane total hydrocarbons analysis apparatus of claim 2, characterized in that a second flow control system is disposed at the pipeline between the second air source and the second air admission hole.

4. The non-methane total hydrocarbons analysis apparatus of claim 3, characterized in that the detector is a hydrogen flame ionization detector, wherein the analysis apparatus further comprises a hydrogen gas source and a detection air source which are connected to the detector.

5. The non-methane total hydrocarbons analysis apparatus of claim 3, characterized in that the molecular sieve filling pipe has therein a molecular sieve with an effective aperture of 5 Å.

6. The non-methane total hydrocarbons analysis apparatus of claim 2, characterized in that the detector is a hydrogen flame ionization detector, wherein the analysis apparatus further comprises a hydrogen gas source and a detection air source which are connected to the detector.

7. The non-methane total hydrocarbons analysis apparatus of claim 2, characterized in that the molecular sieve filling pipe has therein a molecular sieve with an effective aperture of 5 Å.

8. The non-methane total hydrocarbons analysis apparatus of claim 1, characterized in that the detector is a hydrogen flame ionization detector, wherein the analysis apparatus further comprises a hydrogen gas source and a detection air source which are connected to the detector.

9. The non-methane total hydrocarbons analysis apparatus of claim 1, characterized in that the molecular sieve filling pipe has therein a molecular sieve with an effective aperture of 5 Å.

10. The non-methane total hydrocarbons analysis apparatus of claim 1, characterized in that a first flow control system is disposed at the pipeline between the multi-pass valve interface and the six-pass valve interface.

11. The non-methane total hydrocarbons analysis apparatus of claim 10, characterized in that an air pneumatic pump is disposed at the pipeline between the multi-pass valve interface and the first flow control system.

12. The non-methane total hydrocarbons analysis apparatus of claim 11, characterized in that a back pressure valve provided with a shunting exhaust vent is disposed at the pipeline between the air pneumatic pump and the first flow control system.

13. The non-methane total hydrocarbons analysis apparatus of claim 10, characterized in that the detector is a hydrogen flame ionization detector, wherein the analysis apparatus further comprises a hydrogen gas source and a detection air source which are connected to the detector.

14. The non-methane total hydrocarbons analysis apparatus of claim 10, characterized in that the molecular sieve filling pipe has therein a molecular sieve with an effective aperture of 5 Å.

15. A non-methane total hydrocarbons analysis method comprising the steps of:
providing a non-methane total hydrocarbons analysis apparatus including a six-pass valve, a quantification ring, a first stored gas pipe, a second stored gas pipe, a multi-pass valve, a molecular sieve filling pipe, a first air source and a detector,
the six-pass valve having a sample entering hole, a multi-pass valve interface, a quantification ring first interface, a first stored gas pipe outlet, a second stored gas pipe interface and a quantification ring second interface,
the multi-pass valve comprising a first air admission hole, a first discharge hole, a six-pass valve interface, a molecular sieve first interface, a molecular sieve second interface and a first stored gas pipe inlet,
the quantification ring second interface, the quantification ring and the quantification ring first interface being in communication successively,
the multi-pass valve interface being in communication with the six-pass valve interface through a pipeline, the molecular sieve first interface, the molecular sieve filling pipe and the molecular sieve second interface being in communication successively through a pipeline,
the first stored gas pipe inlet, the first stored gas pipe, the first stored gas pipe outlet, the second stored gas pipe interface, the second stored gas pipe and the detector being in communication successively through a pipeline, the first air source being in communication with the first air admission hole,
the six-pass valve having a load status bit and an entered sample status bit, with the load status bit allowing the sample entering hole to be in communication with the quantification ring second interface, the multi-pass valve interface being in communication with the quantification ring first interface, and the first stored gas pipe outlet being in communication with the second stored gas pipe interface, and with the entered sample status bit allowing the sample entering hole being in communication with the multi-pass valve interface, the quantification ring first interface being in communication with the first stored gas pipe outlet, and the second stored gas pipe interface being in communication with the quantification ring second interface,
the multi-pass valve having a load status bit and an entered sample status bit, with the load status bit allowing the first air admission hole being in communication with the first discharge hole, the six-pass valve interface being in communication with the molecular sieve first interface, and the molecular sieve second interface being in communication with the first stored gas pipe inlet, and with the entered sample status bit allowing the first discharge hole being in communication with the six-pass valve interface, and the first stored gas pipe inlet being in communication with the first air admission hole;
configuring the six-pass valve and the multi-pass valve to have the load status bit each, conveying a gas under test from the sample entering hole to the six-pass valve, passing the gas through the quantification ring second interface and the quantification ring successively to thereby fill the quantification ring with the gas, conveying the gas from the quantification ring first interface to the six-pass valve, conveying the gas to the six-pass valve interface through the multi-pass valve interface, conveying the gas to a molecular sieve filling pipe through the molecular sieve first interface, wherein non-methane total hydrocarbons in the gas are adsorbed and filtered out by the molecular sieve to therefore produce a background gas which contains methane hydrocarbons only, and then the background gas enters the multi-pass valve again through the molecular sieve second interface, enters the first stored gas pipe through the first stored gas pipe inlet, and fills the first stored gas pipe, wherein, thereafter, the background gas passes through the first stored gas pipe outlet and the second stored gas pipe interface successively, enters the second stored gas pipe, fills the second stored gas pipe and eventually enters the detector; and configuring six-pass valve and the multi-pass valve to have the entered sample status bit each, passing a zero-grade air from the first air source to the multi-pass valve through the first air admission hole, conveying the zero-grade air to the detector through the first stored gas pipe inlet, the first stored gas pipe, the first stored gas pipe outlet, the quantification ring first interface, the quantification ring, the quantification ring second interface, the second stored gas pipe interface, and the second stored gas pipe successively, conveying the background gas from the second stored gas pipe to the detector, conveying the gas under test from the quantification ring to the detector, and conveying the background gas from the first stored gas pipe to the detector, such that the background gas which contains methane hydrocarbons only is detected to thereby function as a baseline of a non-methane total hydrocarbons chromatographic peak.

16. The non-methane total hydrocarbons analysis method of claim 15, wherein the multi-pass valve is an eight-pass valve provided with the second discharge hole and the second air admission hole, the analysis apparatus further comprises a second air source in communication with the second air admission hole;

wherein the load status bit of the eight-pass valve allows the second discharge hole being in communication with the second air admission hole, and the entered sample status bit of the eight-pass valve allows the molecular sieve first interface being in communication with the second discharge hole and allows the second air admission hole being in communication with the molecular sieve second interface.

17. The non-methane total hydrocarbons analysis method of claim 16, characterized in that: the zero-grade air of the second air source is conveyed to the multi-pass valve through the second air admission hole and conveyed to molecular sieve through the molecular sieve second interface to thereby perform reverse decomposition on the molecular sieve, remove the adsorbed non-methane total hydrocarbons, and discharge the non-methane total hydrocarbons-containing air through the molecular sieve first interface and the second discharge hole.

18. The non-methane total hydrocarbons analysis method of claim 4, wherein a second flow control system is disposed at the pipeline between the second air source and the second air admission hole.

19. The non-methane total hydrocarbons analysis method of claim 18, characterized in that: the zero-grade air of the second air source is conveyed to the multi-pass valve through the second air admission hole and conveyed to molecular sieve through the molecular sieve second interface to thereby perform reverse decomposition on the molecular sieve, remove the adsorbed non-methane total hydrocarbons, and discharge the non-methane total hydrocarbons-containing air through the molecular sieve first interface and the second discharge hole.

20. The non-methane total hydrocarbons analysis method of claim 18, wherein the detector is a hydrogen flame ionization detector, wherein the analysis apparatus further comprises a hydrogen gas source and a detection air source which are connected to the detector.

21. The non-methane total hydrocarbons analysis method of claim 20, characterized in that: the zero-grade air of the second air source is conveyed to the multi-pass valve through the second air admission hole and conveyed to molecular sieve through the molecular sieve second interface to thereby perform reverse decomposition on the molecular sieve, remove the adsorbed non-methane total hydrocarbons, and discharge the non-methane total hydrocarbons-containing air through the molecular sieve first interface and the second discharge hole.

22. The non-methane total hydrocarbons analysis method of claim 18, wherein a second flow control system is disposed at the pipeline between the second air source and the second air admission hole;

wherein the molecular sieve filling pipe has therein a molecular sieve with an effective aperture of 5 Å.

23. The non-methane total hydrocarbons analysis method of claim 22, characterized in that: the zero-grade air of the second air source is conveyed to the multi-pass valve through the second air admission hole and conveyed to molecular sieve through the molecular sieve second interface to thereby perform reverse decomposition on the molecular sieve, remove the adsorbed non-methane total hydrocarbons, and discharge the non-methane total hydrocarbons-containing air through the molecular sieve first interface and the second discharge hole.

24. The non-methane total hydrocarbons analysis method of claim 16, wherein the detector is a hydrogen flame ionization detector, and the analysis apparatus further comprises a hydrogen gas source and a detection air source which are connected to the detector.

25. The non-methane total hydrocarbons analysis method of claim 24, characterized in that: the zero-grade air of the second air source is conveyed to the multi-pass valve through the second air admission hole and conveyed to molecular sieve through the molecular sieve second interface to thereby perform reverse decomposition on the molecular sieve, remove the adsorbed non-methane total hydrocarbons, and discharge the non-methane total hydrocarbons-containing air through the molecular sieve first interface and the second discharge hole.

26. The non-methane total hydrocarbons analysis method of claim 16, wherein the molecular sieve filling pipe has therein a molecular sieve with an effective aperture of 5 Å.

27. The non-methane total hydrocarbons analysis method of claim 26, characterized in that: the zero-grade air of the second air source is conveyed to the multi-pass valve through the second air admission hole and conveyed to molecular sieve through the molecular sieve second interface to thereby perform reverse decomposition on the molecular sieve, remove the adsorbed non-methane total hydrocarbons, and discharge the non-methane total hydrocarbons-containing air through the molecular sieve first interface and the second discharge hole.

28. The non-methane total hydrocarbons analysis method of claim 15, wherein the detector is a hydrogen flame ionization detector;

wherein the analysis apparatus further comprises a hydrogen gas source and a detection air source which are connected to the detector.

29. The non-methane total hydrocarbons analysis method of claim 15, wherein the molecular sieve filling pipe has therein a molecular sieve with an effective aperture of 5 Å.

30. The non-methane total hydrocarbons analysis method of claim 15, wherein a first flow control system is disposed at the pipeline between the multi-pass valve interface and the six-pass valve interface;
   wherein an air pneumatic pump is disposed at the pipeline between the multi-pass valve interface and the first flow control system.

31. The non-methane total hydrocarbons analysis method of claim 30, wherein a back pressure valve provided with a shunting exhaust vent is disposed at the pipeline between the air pneumatic pump and the first flow control system.

32. The non-methane total hydrocarbons analysis method of claim 15, wherein a first flow control system is disposed at the pipeline between the multi-pass valve interface and the six-pass valve interface;
   wherein the detector is a hydrogen flame ionization detector, wherein the analysis apparatus further comprises a hydrogen gas source and a detection air source which are connected to the detector.

33. The non-methane total hydrocarbons analysis method of claim 15, wherein a first flow control system is disposed at the pipeline between the multi-pass valve interface and the six-pass valve interface;
   wherein the molecular sieve filling pipe has therein a molecular sieve with an effective aperture of 5 Å.

34. The non-methane total hydrocarbons analysis method of claim 15, wherein a first flow control system is disposed at the pipeline between the multi-pass valve interface and the six-pass valve interface.

\* \* \* \* \*